United States Patent
Campbell et al.

(10) Patent No.: US 10,167,397 B2
(45) Date of Patent: *Jan. 1, 2019

(54) METHOD TO DETERMINE CONNECTOR METAL WEAR VIA FLUORESCENCE

(71) Applicant: International Business Machines Corporation, Armonk, NY (US)

(72) Inventors: Eric J. Campbell, Rochester, MN (US); Sarah K. Czaplewski, Rochester, MN (US); Joseph Kuczynski, North Port, FL (US); Timothy J. Tofil, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/833,467

(22) Filed: Dec. 6, 2017

(65) Prior Publication Data

US 2018/0095038 A1    Apr. 5, 2018

Related U.S. Application Data

(63) Continuation of application No. 15/285,404, filed on Oct. 4, 2016, now Pat. No. 9,885,659.

(51) Int. Cl.
  *G01N 21/64* (2006.01)
  *C09D 5/22* (2006.01)
  *G01N 31/22* (2006.01)

(52) U.S. Cl.
  CPC .............. *C09D 5/22* (2013.01); *G01N 31/22* (2013.01)

(58) Field of Classification Search
  CPC ............. G01N 21/8422; H01H 1/0015; H01H 2001/0026; H01H 2001/0031
  See application file for complete search history.

(56) References Cited

U.S. PATENT DOCUMENTS

| 4,929,837 A | 5/1990 | DiVita et al. |
| 6,344,171 B1 * | 2/2002 | Nomura .................... C22C 9/00 148/433 |

(Continued)

FOREIGN PATENT DOCUMENTS

JP    H10123067 A    5/1998

OTHER PUBLICATIONS

M. Santra et al., "Fluorescent detection of palladium species with an O-propargylated fluorescein," Chem. Commun., 2010, vol. 46, pp. 3964-3966.
J. Jiang et al., "Acolorimetric and Ratiometric Fluorescent Probe for Palladium," Organic Letters, 2011, vol. 13, No. 18, pp. 4922-4925.
A. Banerjee et al., "Nickel(II)-induced Excimer Formation of a Naphthalene-based Fluorescent Probe for Living Cell Imaging," Inorg. Chem., 2012, vol. 51, pp. 5699-5704.

(Continued)

*Primary Examiner* — Kiho Kim
(74) *Attorney, Agent, or Firm* — Patterson + Sheridan, LLP

(57) ABSTRACT

Method and apparatus for determining a quality or characteristic of connectors in electronic components is provided. Methods include applying a UV-responsive indicator solution active for Pd, Ni, or Cu to a connector on an electrical component; irradiating the connector with UV radiation; detecting a response to the UV radiation; and determining a quality of the connector based on the response to the UV radiation. Apparatus includes an enclosure; a support; a dispenser oriented toward the substrate support; a source of UV-responsive indicator solution active for Pd, Ni, or Cu ions fluidly coupled to the dispenser; a UV source coupled to the enclosure; and a radiation sensor positioned to detect light inside the enclosure.

15 Claims, 3 Drawing Sheets

(56) References Cited

U.S. PATENT DOCUMENTS

| | | | |
|---|---|---|---|
| 6,361,205 B2 | 3/2002 | Andersen | |
| 6,777,948 B2 | 8/2004 | Dominelli et al. | |
| 6,864,489 B2 | 3/2005 | Chen et al. | |
| 6,884,998 B2 | 4/2005 | Nichols | |
| 7,038,201 B2 | 5/2006 | Nichols | |
| 7,053,625 B2 | 5/2006 | Dominelli et al. | |
| 7,368,743 B2 | 5/2008 | Nichols | |
| 9,329,238 B1 | 5/2016 | Carson et al. | |
| 2008/0011724 A1* | 1/2008 | Acker | C03B 33/091 219/121.69 |
| 2012/0107184 A1* | 5/2012 | Asiyanbola | A61L 2/04 422/119 |
| 2014/0242623 A1 | 8/2014 | Phillips et al. | |

OTHER PUBLICATIONS

H. Wang, et al., "Nickel(II) and iron(III) selective off-on-type fluorescence probes based on perylene tetracarboxylic diimide†‡," Org. Biomol. Chem., 2010, vol. 8, pp. 1017-1026.

Molecular Probes Handbook, 11th Edition (2010), Chapter 19, pp. 829-882.

A. Garner and K. Koide, "Studies of a fluorogenic probe for palladium and platinum leading to a palladium-specific detection method†," Chem. Commun., 2009, pp. 86-88.

U.S. Appl. No. 15/285,404 entitled "Method to Determine Connector Metal Via Flourescence," filed Oct. 4, 2016.

IBM, "List of IBM Patents or Patent Applications Treated as Related," for U.S. Appl. No. 15/833,467, filed Feb. 27, 2018.

* cited by examiner

METHOD TO DETERMINE CONNECTOR METAL WEAR VIA FLUORESCENCE

CROSS-REFERENCE TO RELATED APPLICATIONS

This application is a continuation of co-pending U.S. patent application Ser. No. 15/285,404, filed Oct. 4, 2016. The aforementioned related patent application is herein incorporated by reference in its entirety.

BACKGROUND

The present invention relates to manufacturing of electronic components, and more specifically to methods of determining reliability of electronic components. Connector wear in the IT industry is a major concern due to the exposure of the underlying layers to the environment that may cause corrosion. The exposure of the underlying layers is typically due to mechanical wear from excess cycles of plugging the connector into a receptacle, or can be associated with shock and vibration in connection with processes such as shipping. When qualifying connector wear, shock, vibration, and plugging are used to first "damage" the contacts, which are typically made of gold over nickel (or palladium and nickel) over copper. Once the wear processes have been completed, an evaluation of the exposed metals must be done via optical inspection and scanning electron microscopy (SEM), and energy dispersive spectroscopy (EDS) analysis, which often requires destructive sectioning of the electronic component. New methods and apparatus are needed to detect excessive wear in electronic connectors that are more portable, less costly and time consuming, and do not require that the electronic component be destroyed.

SUMMARY

Embodiments described herein provide methods of processing an electrical component, comprising: applying a UV-responsive indicator solution active for Pd, Ni, or Cu to a connector on an electrical component; irradiating the connector with UV radiation; detecting a response to the UV radiation; and registering failure of the connector based on the response to the UV radiation.

Other embodiments described herein provide an apparatus, comprising: an enclosure; a support; a dispenser oriented toward the substrate support; a source of UV-responsive indicator solution active for Pd, Ni, or Cu fluidly coupled to the dispenser; a UV source coupled to the enclosure; and a radiation sensor positioned to detect light inside the enclosure.

DETAILED DESCRIPTION

This disclosure contains, and may claim, chemical structures that denote atomic composition of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals forces, isoelectronic surfaces, and the like may vary among instances of the same chemical compound. Additionally, unless otherwise noted, the disclosed structures cover all stereoisomers of the represented compounds.

Figure 1:
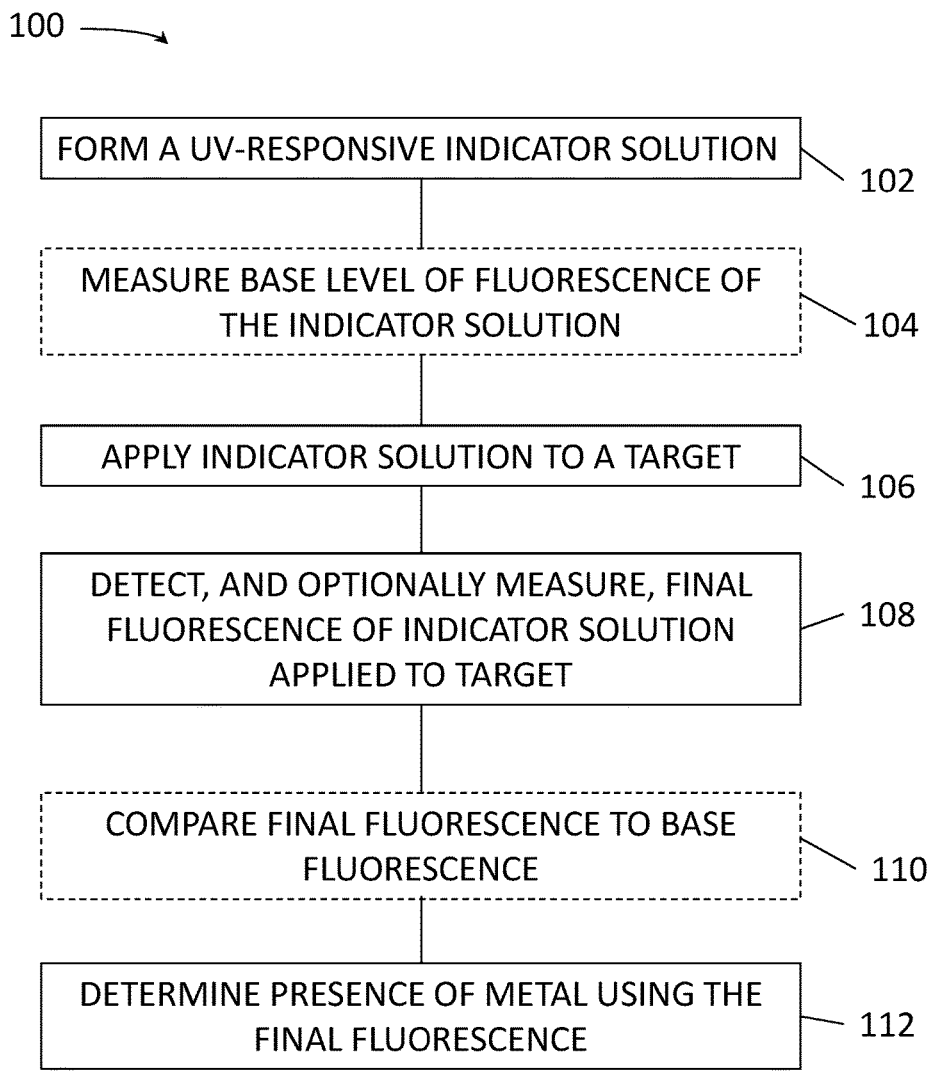
FIG. 1 is an operation diagram illustrating a method according to one embodiment.

FIG. 1 is an operation diagram illustrating a method 100 according to one embodiment. The method 100 is used to detect excessive wear that can lead to failure of connections in electrical components by detecting exposure of metals used in the connections. A UV-responsive chemical indicator active for metals in the connections of the electrical component can be used to detect when those metals are exposed. Compounds that complex with species of palladium (Pd), nickel (Ni), and/or copper (Cu) such that the complex has changed behavior when irradiated by UV radiation can be used to indicate the presence of those metals, and such compounds can be applied to electrical connectors to determine when the gold plated coating on the connectors has worn, cracked, or otherwise failed exposing the underlying metals.

A UV-responsive indicator solution is formed at 102. Depending on the indicator species in the solution, a base level of fluorescence is optionally measured at 104. The solution is irradiated with radiation at a target excitation wavelength to stimulate fluorescence, and the intensity of the visible emission is measured. At 106, the UV-responsive indicator solution is applied to a target, such as an electrical contact. If the solution contacts any metals for which the solution is active, as explained further below, the spectrophotometric response of the indicator will change. In some cases, the base solution does not fluoresce while the applied solution fluoresces in the presence of metals. In other cases, the fluorescence changes from a base fluorescence of the indicator solution alone to a final fluorescence in the presence of certain metals. At 108, the final fluorescence of the indicator solution applied to the target is detected, and optionally quantified. In cases where the fluorescence changes from a base level to a final level, the final fluorescence is optionally compared to the base fluorescence at 110, and at 112, presence of metal is determined using the final fluorescence. In cases where the base solution does not fluoresce prior to exposure to the target, merely detecting fluorescence of the solution after applying to the target indicates the presence of metals.

Figure 2:
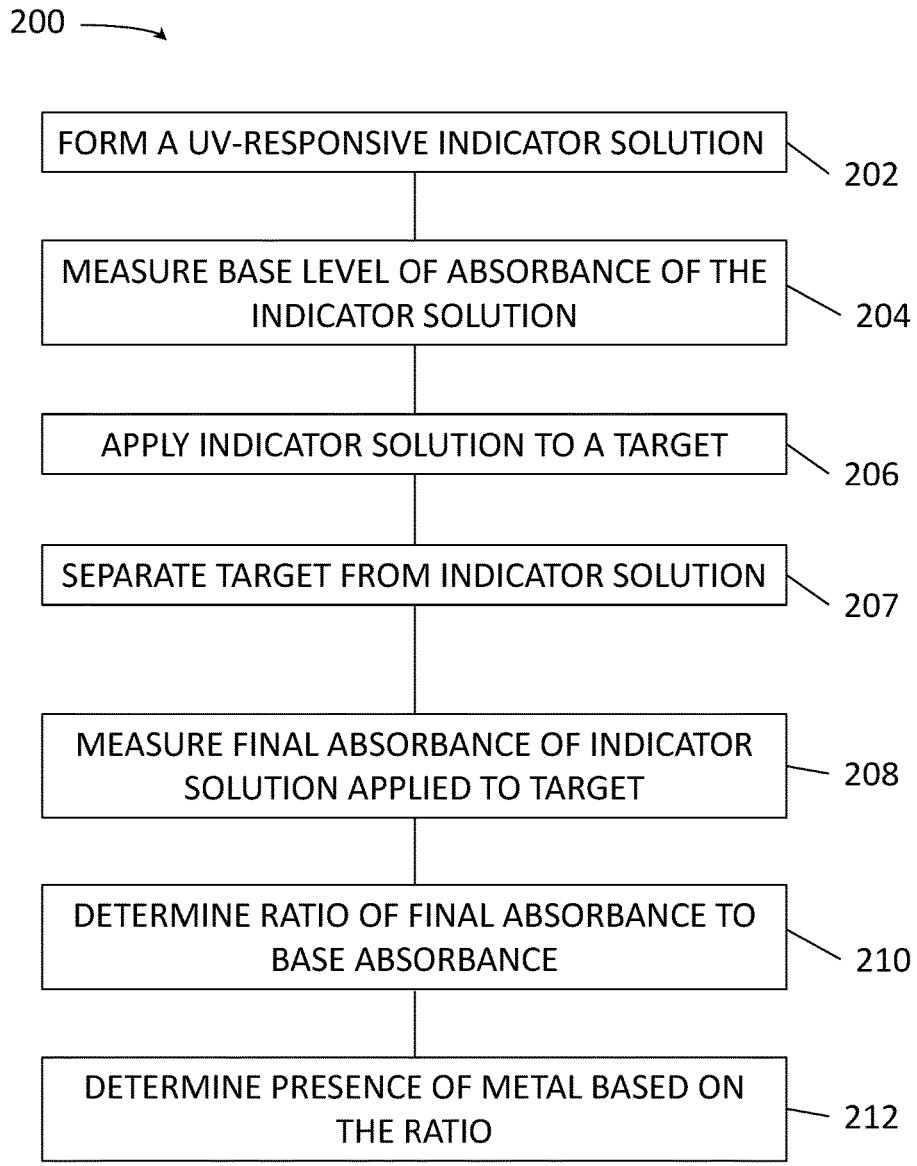
FIG. 2 is an operation diagram illustrating a method according to another embodiment.

FIG. 2 is a flow diagram illustrating a method 200 according to another embodiment. The method 200 differs from the method 100 in that presence of metal is detected, not by measuring fluorescence of the indicator when applied to the target, but by measuring the change or lack of change in absorbance of radiation by the indicator after exposure to the target. A UV-responsive indicator solution is formed at 202, and a base absorbance is measured at 204, for example by US/visible spectrophotometry. The UV-responsive indicator solution is the applied to a target, such as an electrical contact, at 206. After a set amount of time, the target is separated from the solution at 207. At 208, final absorbance of the solution is measured after application to the target, and a ratio of the absorbance after application to the target to the base absorbance is determined at 210. At 212, presence of exposed metal is determined based on the ratio, for example if the ratio is below a threshold value. For indicators with absorbance spectra active for specific species, a ratio below about 80% typically indicates exposure of the indicated metals in the target, for example exposure of underlying metals in an electrical contact.

In both the method 100 and the method 200, and other embodiments, the target can be rinsed following analysis using the indicator solution, dried, and then reused. The methods described herein do not require destructive analysis of the target. Rinsing or washing the target with a solvent such as alcohol (e.g. isopropyl alcohol) after analysis can remove any residual indicator solution. The target can then be dried and reused.

For best accuracy in detecting presence of metals on an electrical contact using a UV absorbance active indicator, a sample of the electronic contact to be measured that is known to meet specifications, or otherwise is of known quality, is exposed to the indicator solution, and the absorbance spectrum of the solution measured, for example by US/visible spectrophotometry. When another such electronic component of unknown quality is measured, the resulting absorbance can be compared with the base absorbance to determine relative quality of the tested component. As noted above, a ratio of the absorbances can be used to determine presence of indicated metals.

In some cases, standard curves or relationships may be defined by exposing one or more known articles or compositions to a known indicator solution. The responses can be quantified and related to properties of the known articles or compositions. Responses in fluorescence and/or absorbance may be used. The standard curves or relationships can then be used to quantify, or at least classify, responses observed in connection with articles of unknown character.

The UV-responsive indicator solution comprises at least one compound selected from the group consisting of compound 1, compound 2, compound 3, compound 4, compound 5, and compound 6 having the following structures:

compound 1

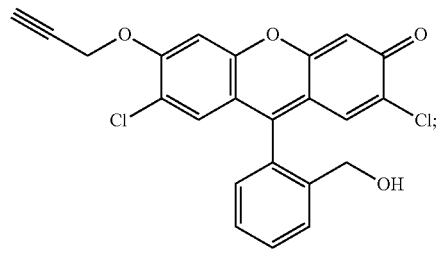

compound 2

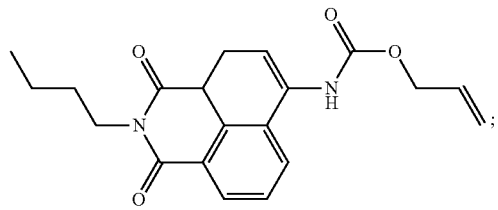

compound 3

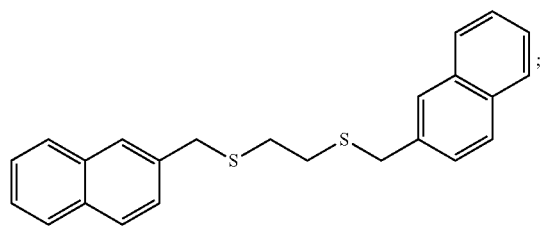

compound 4

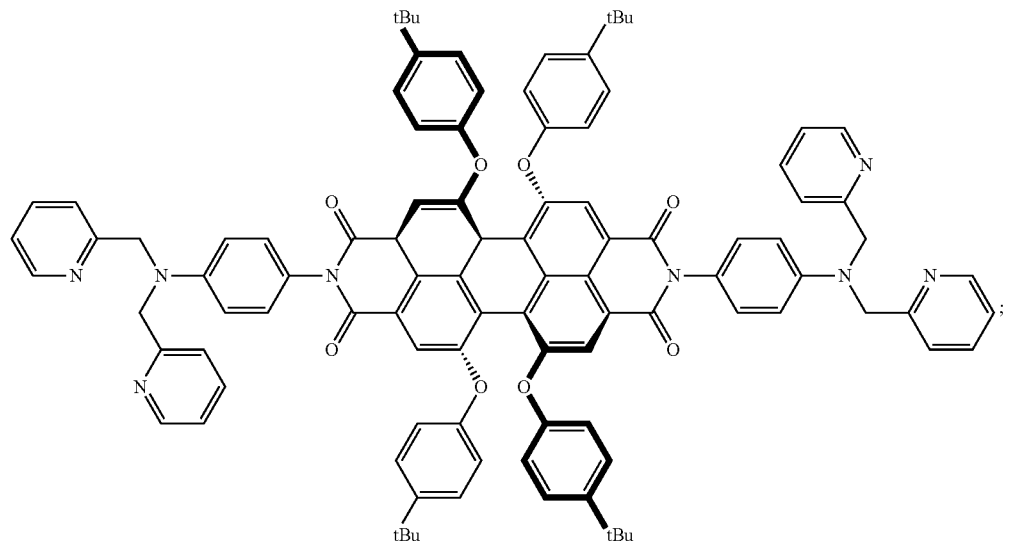

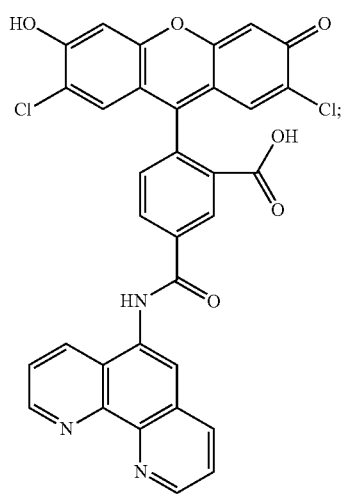

compound 5

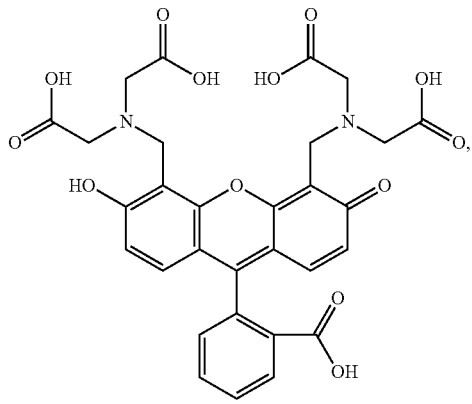

compound 6 or ions thereof. One or more such compounds may be included in the solution. The compounds are dissolved in an appropriate solvent, which may be a polar solvent such as water, dimethylsulfoxide (DMSO), or dimethylformamide (DMF), and which may include other solvents such as hydrocarbons, alcohols, esters, carboxylic acids, and the like.

Compounds 1-6 are UV-responsive in that each of the compounds absorbs UV radiation at some wavelength within the UV spectrum in the presence or absence of certain metal species. Compounds 1-6 additionally fluoresce at various wavelengths when excited by UV radiation at their respective absorbance wavelengths. Compounds 1-6 are also active for various metals, in particular Pd, Ni, and Cu, and their UV response changes in the presence of those metals. The compounds can thus be used to indicate the presence or absence of the metals. For example, UV absorbance of the UV-responsive indicator solution can be measured by UV/visible spectrophotometry. The solution can be contacted with a metal source, and then the UV absorbance of the solution can be measured after contacting with the metal source to determine whether the UV response of the solution has changed. Alternately, fluorescence of the solution before and/or after contacting with the metal source can be detected and/or measured to determine the presence of specific metals.

Compound 1, for example, is active for Pd, forming compound 1A below by catalytic depropargylation in the presence of Pd species:

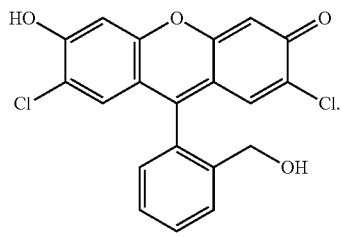

compound 1A

While compound 1 fluoresces only weakly, compound 1A absorbs radiation of wavelength 480 nm and emits radiation of wavelength 520 nm, with quantum efficiency reported as 0.89. A solution of compound 1 in water, optionally including other solvents, can be used to detect the presence of Pd at any valence state, specifically Pd(0), Pd(II), and Pd(IV). The concentration of compound 1 in the solution is not particularly limited, and concentrations as low as 1 mM can be used with appropriate detection equipment. Typical solutions will be 5 mM, 10 mM, 15 mM, or 20 mM in concentration of compound 1 in solvent, for example water.

Compound 1 can be made in a two-step synthesis. In the first step, commercially available 2,7-dichlorofluorescein is added to propargyl bromide and $K_2CO_3$ in DMF at 60° C. The resulting intermediate is isolated, for example by drying and solvent extraction, and then dissolved in dimethylformamide (DMF). The mixture is cooled to −78° C., for example using a liquid nitrogen bath, and diisobutylaluminum hydride (DIBAL-H) is added. The mixture is allowed to react while the temperature rises to room temperature, and then 2,3-dichloro-5,6-dicyano-1,4-benzoquinone (DDQ) is added to complete the reaction. The resulting product may be isolated by drying and solvent extraction or purification.

Compound 2 (N-butyl-4-NHAlloc-1,8-naphthalimide) is also active for Pd(0), Pd(II), and Pd(IV), forming compound 2A below by catalytic removal of butenoate in the presence of Pd:

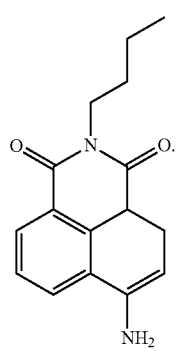

compound 2A

It is believed that the transformation proceeds in two steps, with a deallylation, which may be promoted by the presence of a nucleophile such as morpholine, followed by decarboxylation to yield compound 2A. Compound 2 absorbs UV radiation at a wavelength of 370 nm and emits peak radiation (fluorescence) at a wavelength of 462 nm. Compound 2A absorbs radiation at a wavelength of 430 nm and has peak emission (fluorescence) at a wavelength of 524 nm. An isoemission wavelength for compounds 2 and 2A exists at 498 nm. Thus, compound 2 converts to compound 2A according to the content of Pd in the solution, so compound 2 exhibits a response dependent on the content of Pd. The absorbance at 370 nm declines in relation to the amount of Pd present, the absorbance at 430 nm increases in relation to the amount of Pd present, the emission at 462 nm declines in relation to the amount of Pd present, and the emission at 524 nm increases in relation to the amount of Pd present. It has been reported that compound 2 (by conversion to compound 2A) can detect Pd in concentrations as low as 6.1 nM. Compound 2 can be used in water solution, optionally with acetonitrile or other cosolvents and promoters such as morpholine, at concentrations of 1 mM or higher, for example at concentrations of 5 mM or higher, 10 mM or higher, 15 mM or higher, or 20 mM or higher. Compound 2 can be made from compound 2A by treating compound 2A with allyl chloroformate (2-propenyl chloroformate). Compound 2A may be made, as described in literature, by nitration of acenaphthene, followed by oxidation to the nitro-anhydride, imidation, and reduction to the amine, generally as follows:

Compound 4 is a perylene tetracarboxylic diimide that fluoresces in the presence of $Ni^{2+}$ ions. Compound 4 has two di-(2-picolyl)-amine groups connected to a perylene tetracarboxylic diimide core. Compound 4 absorbs 440 nm radiation in the presence of $Ni^{2+}$ ions and emits radiation at 609 nm, which is enhanced in intensity by the presence of $Ni^{2+}$ ions. The enhancement rises with concentration of $Ni^{2+}$ ions to a maximum of nearly a factor of seven. Thus, the presence of $Ni^{2+}$ can be detected by measuring a base level of fluorescence using compound 4 in a solvent such as DMF, and then applying the solution to a potential source of $Ni^{2+}$ ions, such as an electrical contact, measuring the fluorescence, and comparing the before and after emission intensity.

Compound 4 can be made by condensing 4-dipicolylamino aniline

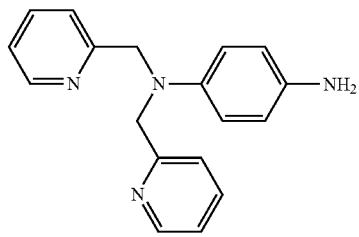 [SMILES: Nc1ccc(N(Cc2ccccn2)Cc2ccccn2)cc1]

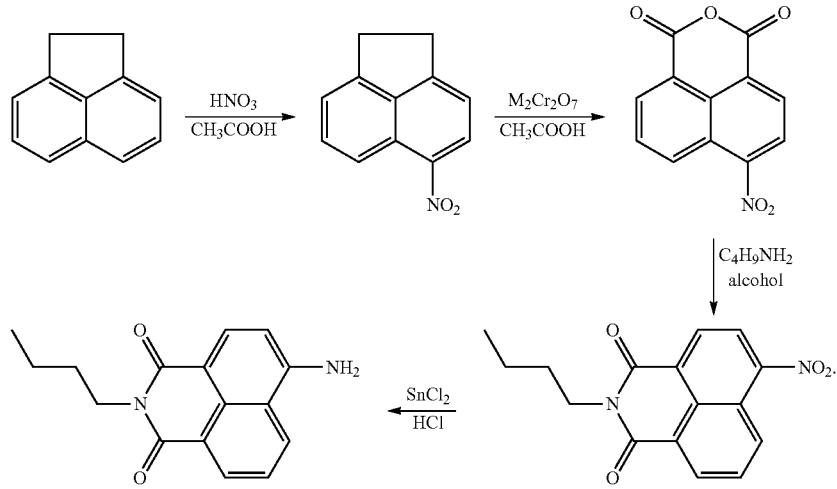

Compound 3 (1-[(naphthalen-3-yl)methylthio]-2-[(naphthalen-6-yl)methylthio]-ethane) is active for Ni, and is thought to form an intramolecular excimer in the presence of Ni. Compound 3 can be used in a solution with water, or other solvents such as DMSO, for example 1:1 by volume water and DMSO. In the presence of $Ni^{2+}$ ions, the complex emits radiation at 430 nm, when exposed to radiation of wavelength 340 nm, with intensity dependent on the concentration of nickel ions in the solution. Concentration of compound 3 in the solution may be 1 mM or higher, for example at concentrations of 5 mM or higher, 10 mM or higher, 15 mM or higher, or 20 mM or higher. Compound 3 can be made by alkylation of ethane-1,2-dithiol using 2-(bromomethyl)-naphthalene under basic conditions (sodium ethanoate in ethanol formed, for example, by dissolving sodium metal in ethanol). Compound 3 can be isolated by drying and solvent extracting using a water-ethyl acetate solution.

with 1,6;7,12-tetra-(4-tert-butylphenoxy)-perylene-3,9:10-tetracarboxylic dianhydride in toluene and imidazole under nitrogen. The aniline precursor can be made by treating aniline with 2-(chloromethyl)-pyridine hydrochloride in aqueous NaOH solution using hexadecyltrimethylammonium chloride as a catalyst to form dipicolylamino benzene. Nitration with silica supported nitric acid in dichloromethane produces a nitro derivative which can be reduced to the dipicolylamino aniline precursor by treatment with $SnCl_2.2H_2O$ in dilute HCl.

Compound 4 can be used as an indicator in DMF solution at concentrations from 1 mM or higher, for example at concentrations of 5 mM or higher, 10 mM or higher, 15 mM or higher, or 20 mM or higher. The base level of fluorescence of a solution of compound 4 is measured at 609 nm, when irradiated with radiation at 440 nm. The solution is then applied to a target, and the fluorescence measured after application to the target. A ratio of intensity after application to base intensity is computed. If the ratio is above 1.1, indicating enhanced fluorescence after application to the target, presence of $Ni^{2+}$ is indicated.

Compound 5 is active for Cu, including both $Cu^+$ and $Cu^{2+}$. Compound 5 is available commercially from Thermo Fisher Scientific Corp. of Waltham, Mass., as Phen Green™ FL indicator, which is a diacetate ester of compound 5, and as Phen Green™SK indicator, which is a dipotassium salt of compound 5. The diacetate ester has been reported as a useful detector for both $Cu^+$ and $Cu^{2+}$, while the dipotassium salt has been reported as a useful indicator of $Cu^+$ using conditions that minimize oxidation of $Cu^+$ to $Cu^{2+}$. The indicators can be used in solutions of water, DMF, DCM, and other solvents described herein at concentrations of 1 mM or higher, for example at concentrations of 5 mM or higher, 10 mM or higher, 15 mM or higher, or 20 mM or higher. Both versions of compound 5 exhibit strong fluorescence quenching in the presence of Cu ions, each reportedly losing over 80% fluorescence intensity relative to metal-free solutions. Use of compound 5, in either form, to detect Cu ions, as described above, is therefore based on measurement of fluorescence intensity of the UV-responsive indicator solution prior to application to the target, and then measurement of fluorescence intensity after application to the target. The two measurements are compared to determine whether fluorescence quenching has occurred, which indicates presence of Cu ions.

Compound 6, commonly referred to as calcein, exhibits fluorescence quenching in the presence of $Cu^{2+}$ ions, with the degree of quenching varying from about 60% to nearly 100% depending on concentration of ions in the solution. Compound 6 can be used in solutions of water, DMF, DCM, and other solvents described herein at concentrations of 1 mM or higher, for example at concentrations of 5 mM or higher, 10 mM or higher, 15 mM or higher, or 20 mM or higher. Compound 6 is commercially available from Sigma Aldrich Corp. of St. Louis, Mo.

Figure 3:
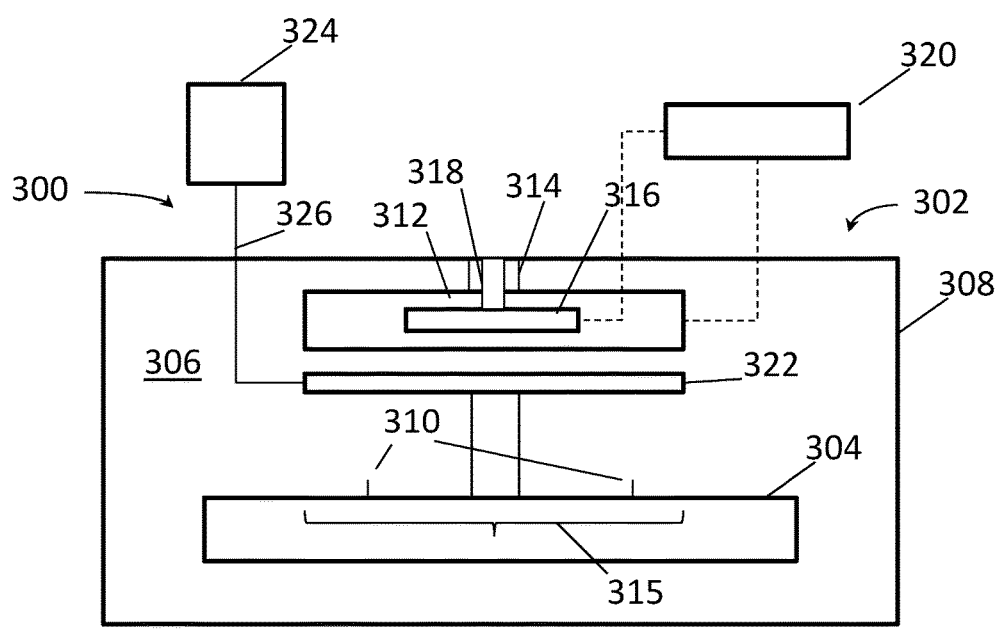
FIG. 3 is a schematic cross-section of an apparatus according to another embodiment.

FIG. 3 is a schematic cross-section of an apparatus 300 according to another embodiment. The apparatus 300 can be used to perform radiant analysis using the solutions and compounds described above. An enclosure 302 encloses a support 304 in a processing volume 306 defined by walls 308 of the enclosure. The enclosure may be substantially, or entirely, light-proof to enhance analytical accuracy and precision. The support 304 generally supports a sample (not shown) in a specified position for analysis using the apparatus 300. The support 304 may be a stationary support, on which the sample, for example an electronic component, is positioned, or the support 304 may be a movable support that carries samples into the enclosure 302 for analysis, and then out of the enclosure 302 after analysis. For example, the support 304 may be, or include, a sample transport member such as a belt actuated by rollers. The support may include positioning guides 310 for positioning the sample on the support 304. Positioning guides may be raised portions, such as walls, pillars, stems, pins, or the like extending from a surface of the support 304.

A UV source 312 is disposed on or in a wall 308 of the enclosure 302, or in the processing volume 306, optionally supported by a support 314, and is positioned to irradiate an area 315 of the support 304 (or more precisely, an area of a sample positioned on the support 304) with UV radiation. The UV source may include one or more UV emitters, each of which may be monochromatic, multichromatic, spectral, and/or broadband. Monochromatic UV sources include UV lasers and LED's. Multichromatic sources include UV laser or LED bars or grids with emitters operating at different wavelengths, or broadband sources radiating through wavelength specific filters. Spectral UV sources include source that emit a spectrum of UV radiation such as discharge emitters (for example lamps such as Hg vapor lamps). Broadband UV sources have broad emission spectra that are broader than emission spectra of individual emitters, typically including more than one spectral emitter. Broadband sources may be broadband laser sources (i.e. UV laser emitters that emit photons across the gain spectrum of the emitter, such as tunable UV lasers and chirped UV lasers) or broadband spectral sources, including sources using two or more types of UV lamps. Power may be coupled to the UV source 312 through an electrical coupling (not shown), which may penetrate the wall 308 of the enclosure 302.

A radiation sensor 316 is disposed on or in a wall 308, which can be the same wall on or in which the UV source 312 is disposed or a different wall, or in the processing volume 306, optionally supported by a support 318. The radiation sensor 316 is positioned to receive radiation from the area 315 of the support. The radiation sensor may be calibrated to sense radiation at the wavelength emitted by the UV source 312 and/or radiation emitted at any of the emission wavelengths. The radiation sensor may be a visible, UV, or near-UV sensor, or may include more than one such sensor to detect multiple wavelengths. The radiation sensor may include a transmission member, such as a light pipe or fiber optic, and may include a spectral analyzer. The radiation sensor 316 senses light at wavelengths emitted by one or more of the indicators described herein, and may also sense the UV radiation emitted by the UV source 312. The radiation sensor 316 may measure intensity of the radiation emitted by one or more of the indicators, and may measure intensity of the UV radiation emitted by the UV source 312. The radiation sensor 316 may compare a measured intensity of indicator radiation to a measured intensity of the UV radiation. The radiation sensor 316 may determine a ratio of the intensity of the indicator radiation to the intensity of the UV radiation. The radiation sensor 316 may use the ratio to determine presence of a metal. For example the radiation sensor 316 may determine the presence of metal if the ratio is below a threshold value, or above a threshold value.

A controller 320 may be coupled to the UV source 312, or to the power supply or power coupling delivering power to the UV source 312, and/or to the radiation sensor 316. The controller 320 may include the spectral analyzer mentioned above. When coupled to the radiation sensor 316, the controller may be configured to register intensity of radiation collected by the radiation sensor 316 at one or more wavelengths. The controller 320 may also be configured to compare radiation detected by the radiation sensor at different wavelengths or at different times, and compute intensity ratios to aid in detection of metals by comparative analysis. The controller 320 may be configured to perform the comparisons and determinations described above in connection with the radiation sensor 316 instead of the radiation sensor 316. For example, the controller 320 may be configured to determine a ratio of the intensity of light detected by the radiation sensor at an indicator wavelength and a standard intensity, compare the ratio to a threshold value, and register an event if the ratio is above the threshold value. The standard intensity may be an intensity of light emitted by an indicator solution prior to exposure to any target. The standard intensity may also be an intensity curve determined as described above.

A dispenser 322 is coupled to the enclosure 302 or the support 304, and is positioned to deliver a material to a specific area 323 of the support 304 substantially coincident with the area 315. The area 323 may be coextensive with the area 315, may overlap the area 315, may be overlapped by the area 315, may surround the area 315, or may be surrounded by the area 315. A source of UV-responsive indicator solution 324, including any or all of the solutions described herein, individually or mixed in any combination as described herein, may be fluidly coupled by a flow pathway 326 to the dispenser 322 by direct connection or by connection to a flow pathway through the enclosure 302. Appropriate flow controls, such as valves and flow meters (not shown), may be provided in the flow pathway.

The apparatus 300 described above may be used to perform any of the methods described herein to facilitate, for example, quality control in an electronic component manufacturing facility.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

While the foregoing is directed to embodiments of the present invention, other and further embodiments of the invention may be devised without departing from the basic scope thereof, and the scope thereof is determined by the claims that follow.

What is claimed is:

1. A method of processing an electrical component, comprising:
   applying a UV-responsive indicator active for Pd, Ni, or Cu to a connector on an electrical component;
   irradiating the UV-responsive indicator applied to the connector with UV radiation;
   detecting a response to the UV radiation; and
   determining a quality of the connector based on the response to the UV radiation comprising:
      determining a ratio of intensity of emitted fluorescent light to intensity of the UV radiation;
      comparing the ratio to a threshold value; and
      registering failure of the connector if the ratio is above the threshold value.

2. The method of claim 1, wherein the UV-responsive indicator comprises a compound selected from the group consisting of compound 1, compound 2, compound 3, compound 4, compound 5, and compound 6 having the following structures:

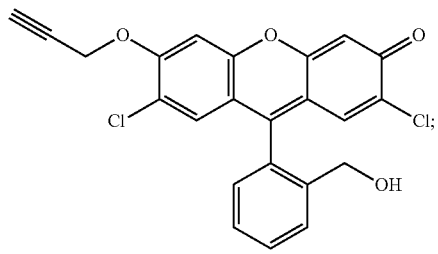

compound 1

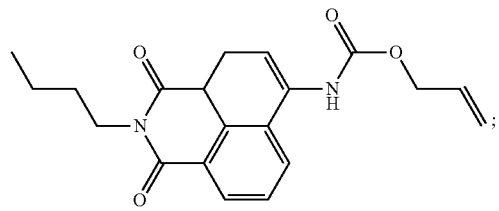

compound 2

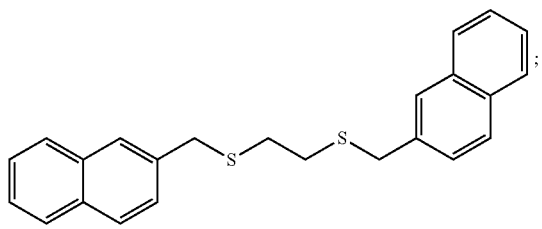

compound 3

-continued

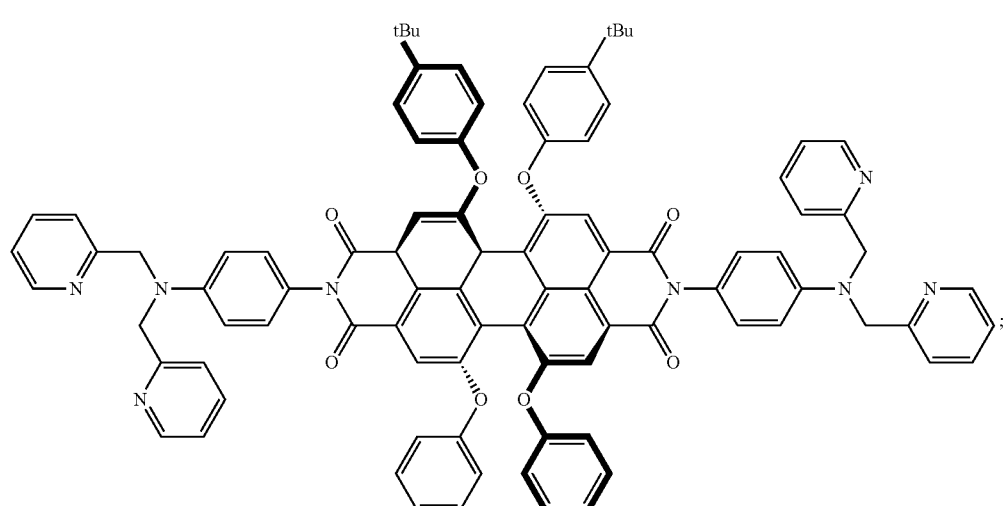
compound 5

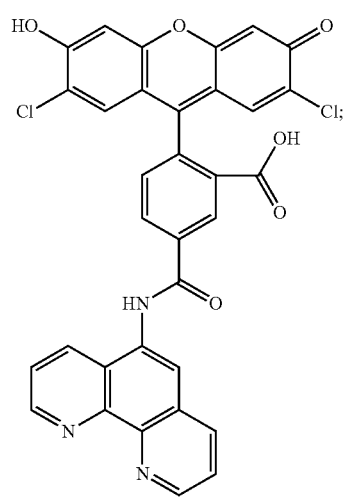

or ions thereof.

3. The method of claim 2, wherein detecting the response to the UV radiation comprises detecting an intensity of fluorescent emission.

4. The method of claim 2, wherein the UV-responsive indicator includes a compound active for Pd, a compound active for Ni, and a compound active for Cu.

5. The method of claim 1, wherein applying the UV-responsive indicator comprises spraying or dipping.

6. The method of claim 1, further comprising, after detecting the fluorescence intensity of the connector, rinsing the connector.

7. The method of claim 1, wherein a plurality of connectors are simultaneously subjected to, at least, the applying, the irradiating, and the detecting.

8. A method of processing an electrical component comprising:
applying a fluorescent indicator solution to a connector on an electrical component, the fluorescent indicator solution comprising a compound selected from the group consisting of compound 1, compound 2, compound 3, compound 4, compound 5, and compound 6 having the following structures:

compound 1

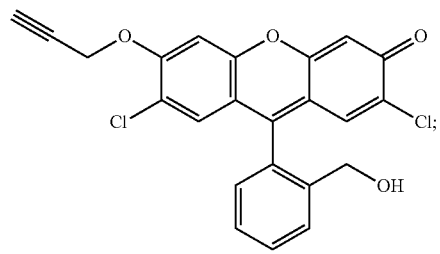

compound 2

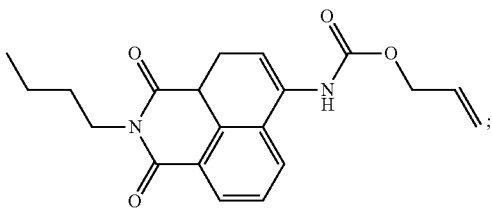

compound 3

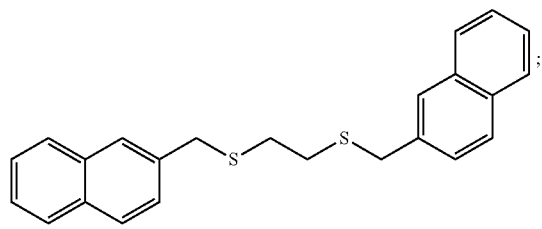

compound 4

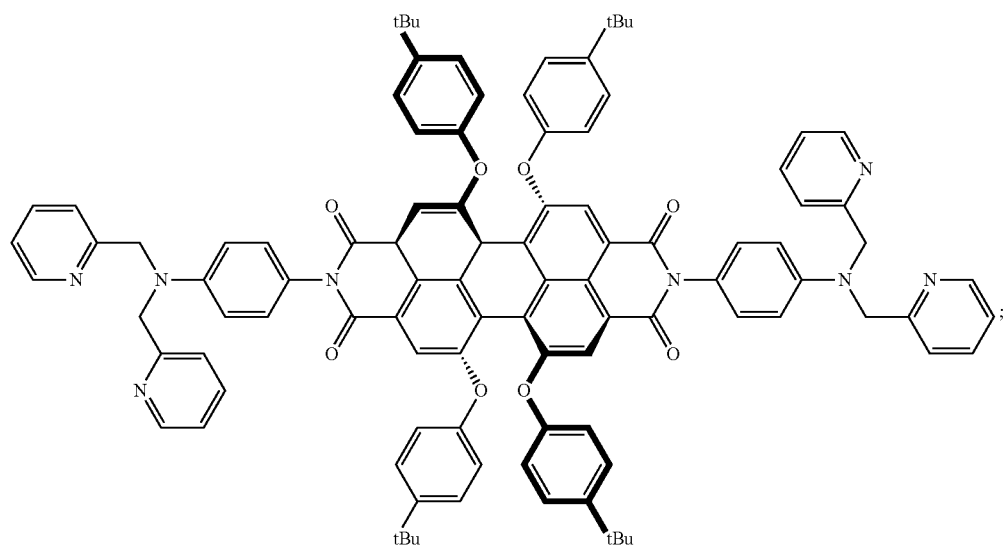

compound 5

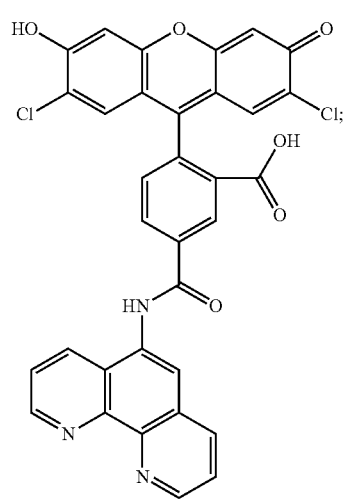

compound 6

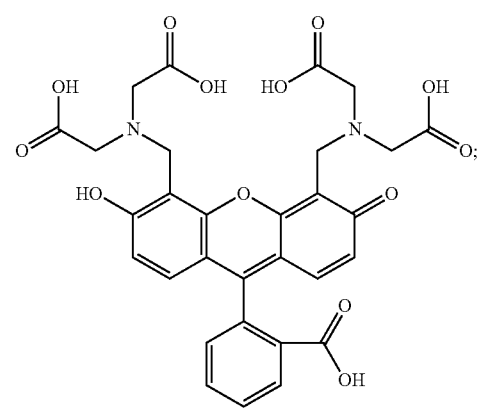

or ions thereof;

irradiating the connector with UV radiation;

detecting a fluorescence intensity of the connector; and determining a quality of the connector based on the fluorescence intensity comprising:

determining an intensity of light emitted by the fluorescent indicator solution prior to applying the fluorescent indicator solution to the connector;

determining an intensity of light emitted by the fluorescent indicator solution after applying the fluorescent indicator solution to the connector;

determining a ratio of intensity of the light emitted by the fluorescent indicator solution before and after applying the fluorescent indicator solution to the connector;

comparing the ratio to a threshold value; and determining that the connector has failed if the ratio is above the threshold value.

9. The method of claim 8, wherein applying the fluorescent indicator solution comprises spraying or dipping.

10. The method of claim 8, wherein the fluorescent indicator solution includes a compound active for each of Pd, Ni, and Cu.

11. The method of claim 8, further comprising, after detecting the fluorescence intensity of the connector, rinsing the connector.

12. An apparatus, comprising:
an enclosure;
a support;
a dispenser oriented toward a substrate support;
a source of UV-responsive indicator active for Pd, Ni, or Cu ions coupled to the dispenser;
a UV source coupled to the enclosure;
a radiation sensor positioned to detect light inside the enclosure; and
a controller configured to determine a ratio of an intensity of light detected by the radiation sensor at an indicator wavelength and a standard intensity, compare the ratio to a threshold value, and register an event if the ratio is above the threshold value.

13. The apparatus of claim 12, wherein the UV-responsive indicator comprises a compound selected from the group consisting of compound 1, compound 2, compound 3, compound 4, compound 5, and compound 6 having the following structures:

compound 1
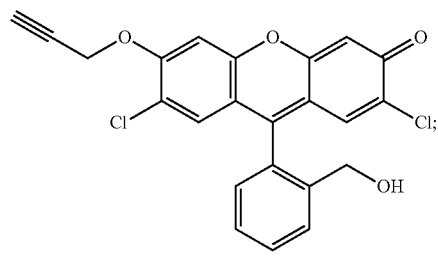

compound 2
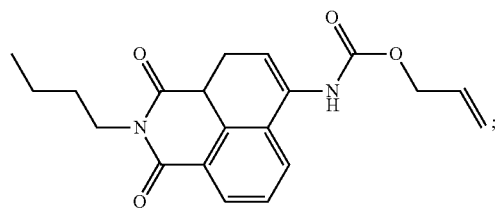

compound 3
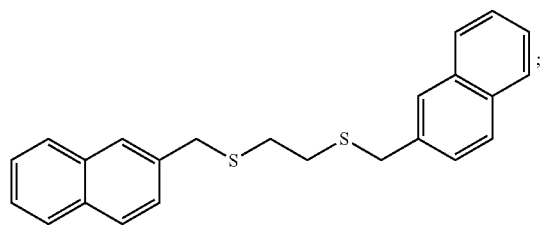

compound 4
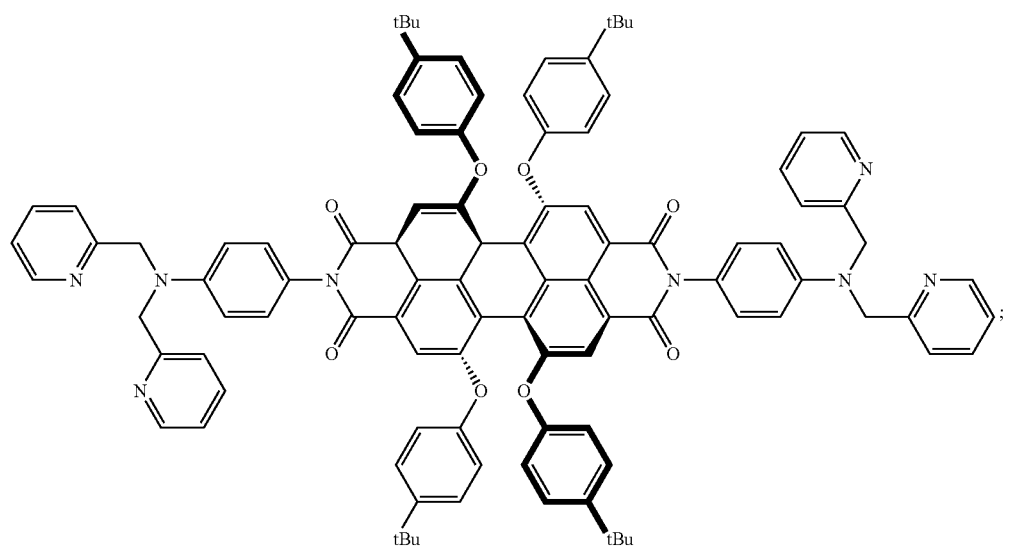

compound 5
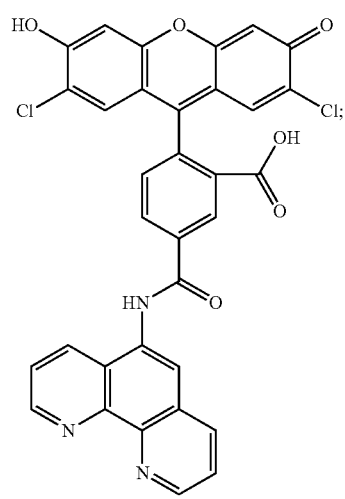
compound 6
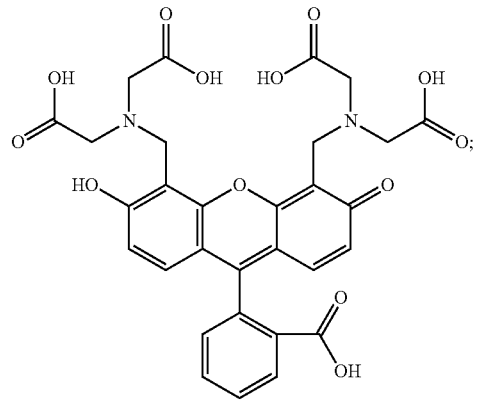
or ions thereof.
14. The apparatus of claim 12, wherein the UV-responsive indicator comprises a compound active for Pd, a compound active for Ni, and a compound active for Cu.
15. The apparatus of claim 12, wherein the radiation sensor is configured to detect light at one or more indicator wavelengths.
* * * * *